US005645763A

United States Patent [19]
Klein et al.

[11] Patent Number: 5,645,763
[45] Date of Patent: Jul. 8, 1997

[54] USE OF LIQUID ESTERS AS SOLVENTS FOR ISOCYANATES

[75] Inventors: Johann Klein, Duesseldorf; Peter Daute, Essen; Roland Gruetzmacher, Wuelfrath; Rainer Hoefer, Duesseldorf, all of Germany

[73] Assignee: Henkel Kommanditgesellschaft auf Aktien, Duesseldorf, Germany

[21] Appl. No.: 339,035

[22] Filed: Nov. 14, 1994

Related U.S. Application Data

[63] Continuation-in-part of PCT/EP93/01104, May 6, 1993.

[51] Int. Cl.$^6$ ............... C09K 3/00; B01F 17/34
[52] U.S. Cl. ............ 252/364; 252/182.2; 252/182.21; 560/330; 137/13
[58] Field of Search ............... 252/364, 182.2, 252/182.21; 560/330, 331; 137/13

[56] References Cited

U.S. PATENT DOCUMENTS

| | | | |
|---|---|---|---|
| 2,801,244 | 7/1957 | Balon | 544/222 |
| 4,067,834 | 1/1978 | Olstowski | 165/151 |
| 4,551,517 | 11/1985 | Herold et al. | 528/60 |
| 4,588,761 | 5/1986 | Thoma et al. | 524/38 |
| 5,034,154 | 7/1991 | Yezrielev et al. | 252/364 |
| 5,136,086 | 8/1992 | Nagata et al. | 560/347 |

FOREIGN PATENT DOCUMENTS 0456062  11/1991  European Pat. Off. .

OTHER PUBLICATIONS

*Hawley's Condensed Chemical Dictionary*, 11th Ed., Definitions for "dodecyl acetate", p. 439; n–octyl acetate, p. 850; methyl stearate, p. 781; methyl laureate, p. 773; methyl caprate, p. 762; and methyl caproate, p. 762, (1987).

*Primary Examiner*—Sharon Gibson
*Assistant Examiner*—Joseph D. Anthony
*Attorney, Agent, or Firm*—Wayne C. Jaeschke; John Daniel Wood; Daniel S. Ortiz

[57] ABSTRACT

The use of esters—liquid at room temperature—of $C_{6-22}$ fatty acids with monohydric alcohols and/or of $C_{6-22}$ fatty alcohols with monocarboxylic acids as solvents for isocyanates and/or isocyanurates is provided. Because the ester reduces the viscosity of the isocyanates and/or isocyanurates, the mixture will be easy to pump and mix with other components prior to curing. Also provided is a process for reducing the viscosity of isocyanates and isocyanurates comprising adding to said isocyanate or isocyanurate one or more esters selected from the group consisting of $C_{6-22}$ fatty acids with monohydric alcohols and $C_{6-22}$ fatty alcohols with monocarboxylic acids, said esters being a liquid at room temperature.

19 Claims, No Drawings

USE OF LIQUID ESTERS AS SOLVENTS FOR ISOCYANATES

CROSS-REFERENCE TO RELATED APPLICATIONS

This application is a continuation-in-part of PCT application PCT/EP93/01104, filed May 6, 1993, the disclosure of which is incorporated by reference.

FIELD OF THE INVENTION

This invention relates to the use of solvents for isocyanates and/or isocyanurates.

BACKGROUND OF THE INVENTION

Isocyanates in the context of the present invention are both conventional isocyanates, which bear NCO groups at aromatic, aliphatic or cycloaliphatic hydrocarbons, and also prepolymers which contain free NCO groups even after reaction of the conventional isocyanates with polyols.

Polyfunctional isocyanates containing two or more NCO groups in particular are highly viscous products. The high viscosity of these products often gives rise to difficulties in the processing of the isocyanates to polyurethanes because the highly viscous isocyanates are difficult to pump and difficult to mix with other components. Accordingly, solvents are added to the isocyanates to reduce their viscosity. Trimeric isocyanurates which are frequently added in the production of polyurethanes are also highly viscous products to which solvents are added to reduce viscosity.

Hitherto, the solvents used have mostly been organic solvents of the halogenated hydrocarbon type, such as methylene chloride, 1,2-dichloropropane; aromatic hydrocarbons, such as toluene; ethers, such as petroleum ether; or even low-viscosity phosphates, such as trioctyl phosphate; trioctyl phosphate also has a plasticizing effect. For ecological and toxicological reasons, however, it is becoming increasingly desirable to replace the unsafe solvents hitherto used by ecologically and toxicologically safer solvents.

It is known from U.S. Pat. No. 2,801,244 that the trifunctional isocyanate trimers of 4-alkyl-m-phenylenediamine diisocyanates can also be dissolved in ethyl acetate. However, ethyl acetate is a highly volatile ester which partly escapes even under the processing conditions.

The problem addressed by the present invention was to provide solvents for isocyanates and isocyanurates which would be toxicologically and ecologically safe and which would be more volatile than ethyl acetate.

SUMMARY OF THE INVENTION

It has surprisingly been found that special esters are capable of drastically reducing the viscosities of isocyanates and isocyanurates, even when added in very small quantities.

Accordingly, the present invention relates to the use of esters—liquid at room temperature—of $C_{6-22}$ fatty acids with monohydric alcohols and/or of $C_{6-22}$ fatty alcohols with monocarboxylic acids as solvents for isocyanates and/or isocyanurates. Because the ester reduces the viscosity of the isocyanates and/or isocyanurates, the mixture will be easy to pump and mix with other components prior to curing. Thus, the mixture will consist essentially of the isocyanate and/or isocyanurate and the ester. In this regard, the mixture will be essentially free of compounds containing active hydrogen and/or catalysts for reaction of the isocyanate and/or isocyanurate with such compounds, either of which may lead to premature reaction of the isocyanate and/or isocyanurate, which premature reaction can increase the viscosity of the isocyanate and/or isocyanurate and thus make the resulting reaction product difficult to pump and difficult to mix with other components.

In one aspect, this invention relates to A composition of matter consisting essentially of a solution of one or more esters selected from the group consisting of $C_{6-22}$ fatty acids with monohydric alcohols and $C_{6-22}$ fatty alcohols with monocarboxylic acids, said esters being a liquid at room temperature, as a solvent for a member selected from the group consisting of isocyanates and isocyanurates.

A group of esters suitable for use in accordance with the invention are esters of $C_{6-22}$ fatty acids with monohydric alcohols. Within this group, esters of aliphatic monohydric alcohols containing 1 to 22 and preferably 1 to 12 carbon atoms are preferred. For the purposes of the invention, both the fatty acids and the alcohols may be saturated and/or unsaturated. If desired, the esters may also contain substituents although the substituents must not be reactive to the isocyanate groups like the reactive hydroxyl groups. Examples of suitable fatty acids are caproic acid, caprylic acid, pelargonic acid, caprio acid, lauric acid, myristic acid, palmitic acid, stearic acid, arachic acid, behenic acid, lauroleic acid, myristoleic acid, palmitoleic acid, oleic acid, linoleic acid and/or linolenic acid and the technical mixtures and fractions thereof which are formed in the hydrolysis and distillation of natural fats and oils. Technical mixtures and fractions of these fatty acids obtainable from coconut oil, palm kernel oil, peanut oil, soybean oil, sunflower oil, linseed oil, rapeseed oil both rich and poor in erucic acid and/or even lard and beef tallow are particularly preferred.

Suitable aliphatic alcohols which are esterified with the fatty acids mentioned above are the branched and unbranched alcohols known from the prior art, such as methanol, ethanol, propanol, butanol, pentanol, 2-ethylhexanol, Guerbet alcohols, and unsaturated representatives or even the fatty alcohols obtainable by hydrogenation of the fatty acids mentioned above. Methyl fatty acid esters are particularly preferred for the purposes of the invention.

The second group of esters suitable for use in accordance with the invention is derived from $C_{6-22}$ fatty alcohols with aliphatic $C_{2-22}$ and preferably $C_{2-12}$ monocarboxylic acids. The fatty alcohols and the aliphatic monocarboxylic acids may be saturated and/or unsaturated. Suitable fatty alcohols are any of those obtainable by hydrogenation of the fatty acids mentioned above. The hydrogenation reaction may be conducted in such a way that any double bonds present in the fatty acids remain intact or are co-hydrogenated so that saturated and/or unsaturated fatty alcohols may be obtained. Suitable aliphatic monocarboxylic acids are acetic acid, propionic acid, butyric acid and pentanoic acid and the fatty acids already listed above. Within this second group of esters, those derived from lower $C_{2-12}$ monocarboxylic acids and from unsaturated alcohols are particularly preferred.

The esters should be liquid at room temperature, i.e. at around 25° C. to 20° C. under normal pressure.

The esters are added to the isocyanates, preferably to the relatively high-viscosity di-, tri- and/or tetraisocyanates, and/or to prepolymers containing 2 to 4 isocyanate groups derived from di-, tri- and/or tetraisocyanates. Of the difunctional and more than difunctional tetraisocyanates, the aromatic representatives are preferred, aromatic diisocyanates, such as 1,5-naphthylene diisocyanate, 4,4'-diphenylmethane diisocyanate, 4,4-diphenyl dimethylmethane diisocyanate, di- and tetraalkyl diphenylmethane diisocyanate, 4,4'-dibenzyl diisocyanate and the isomers of tolylene diisocyanate being particularly preferred. Suitable representatives of tri- and tetraisocyanates are the commercial products, such as Desmodur®VKS, a product of Bayer AG, Voronate®229, a product of Dow Chemical, and/or Basonate®A 270, a product of BASF.

Within the group of isocyanate-containing prepolymers, those obtained by reaction of the above isocyanates with polyols, such as polyether polyols, polyester polyols, polyalkylenediols and/or polyacetals, are preferred. The polyols mentioned and their production are known from the prior art.

For example, polyester polyols may be obtained by reaction of dicarboxylic acids with triols or with an excess of diols and/or triols and by ring opening of epoxidized (fatty) esters with alcohols. Polycaprolactone diols obtainable from ecaprolactone and diols are also suitable as polyester polyols. Preferred polyester polyols for the purposes of the invention are polyester polyols or low molecular weight dicarboxylic acids, such as adipic acid, isophthalic acid, terephthalic acid and phthalic acid, with an excess of diols containing 2 to 12 carbon atoms, trimethylol propane and/or glycerol. Suitable polyacetals are, for example, the polycondensation products of formaldehyde and diols and/or polyols in the presence of acidic catalysts. Polyalkylenediols, such as polybutadiene diol for example, are commercial products which are obtainable in various molecular weights. Polyether polyols may be obtained, for example, by copolymerization or block polymerization of alkylene oxides, such as ethylene oxide, propylene oxide and butylene oxide, or by reaction of polyalkylene glycols with di- or trihydric alcohols. However, the polymerized ring opening products of tetrahydrofuran with alcohols are also suitable as polyether polyols.

According to the invention, the esters may also be added to isocyanurates, the trimeric derivatives of isocyanuric acid, such as tris-(6-isocyanato)-isocyanurate (Tolonate HDT®, a product of Rhône-Poulenc).

Even when added in small quantities, the esters used in accordance with the invention drastically reduce the viscosity of isocyanates and/or isocyanurates, above all to a far greater extent than might be expected from simple dilution effects. Another advantage is that the viscosity of the dilute isocyanates and/or isocyanurates changes very little, if at all, even in the event of prolonged storage, so that isocyanates or isocyanurates diluted with the esters can be safely stored without the ester having to be constantly replenished. Finally, the esters used are also inert to the isocyanates or isocyanurates so that no unwanted secondary reactions occur.

To achieve the required reduction in viscosity, it is best to use the ester in a ratio by weight to the isocyanates/isocyanurates of 5:95 to 95:5. Depending on the required viscosity of the isocyanates/isocyanurates, the expert may readily determine the necessary quantity of ester for himself.

The present invention relates to a process for reducing the viscosity of isocyanates and/or isocyanurates which is characterized in that esters—liquid at room temperature—of $C_{6-22}$ fatty acids with monohydric alcohols and/or of $C_{6-22}$ fatty alcohols with monocarboxylic acids are added to the isocyanates.

Further particulars can be found in the foregoing text.

EXAMPLES

Example 1

Various quantities by weight of a methyl ester of a rapeseed oil fatty acid mixture low in erucic acid (composition in % by weight: 0 to 5 erucic acid ($C_{22}$), 50 to 65 oleic acid ($C_{18}'$), 15 to 30 linoleic acid ($C_{18}''$), 6 to 13 linolenic acid ($C_{18}'''$), 1 to 3 eicosanoic acid ($C_{20}'$), 1 to 4 palmitic acid ($C_{16}$) and traces of myristic acid ($C_{14}$), stearic acid ($C_{18}$), arachic acid ($C_{20}$), behenic acid ($C_{22}$)) were added to 4,4'-diphenylmethane diisocyanate (MDI). The solvent effect was determined from the Höppler viscosity of the mixtures at 20° C. (DIN 53015). The results are set out in Table 1.

TABLE 1

| | Viscosity | |
|---|---|---|
| Methyl ester % by weight | MDI % by weight | Höppler viscosity at 20° C. in [mPa · s] |
| 0 | 100 | 370 |
| 10 | 90 | 137 |
| 20 | 80 | 72 |
| 30 | 70 | 44 |
| 40 | 60 | 29 |
| 50 | 50 | 20 |
| 60 | 40 | 15 |
| 70 | 30 | 12 |
| 80 | 20 | 9 |
| 90 | 10 | 8 |
| 100 | 0 | 6 |

It can be seen from Table 1 that the viscosity of the MDI can be considerably reduced by addition of only a small quantity of the methyl ester.

Example 2

200 g of a methyl ester of a soybean oil fatty acid mixture (composition in % by weight: 7 to 10 palmitic acid ($C_{16}$), 3 to 6 stearic acid ($C_{18}$), 0 to 2 arachic acid ($C_{20}$), 20 to 35 oleic acid ($C_{18}'$), 40 to 57 linoleic acid ($C_{18}''$) and 5 to 15 linolenic acid ($C_{18}'''$)) were added to 446 g of the MDI according to Example 1. The stability of the mixture in storage was tested by observing both the viscosity and the NCO content over a prolonged period. The NCO content was determined by reaction of the mixture with an excess of n-butylamine and back-titration of the unreacted butylamine with hydrochloric acid. The NCO content is determined from the consumption of butylamine. The results are set out in Table 2.

TABLE 2

| | Storage test | | |
|---|---|---|---|
| Days | Höppler viscosity at 20° C. (mPa · s) | NCO content (% by weight) | Visual assessment |
| 0 | 40 | 21.3 | Clear solution |
| 5 | 47 | N.d. | Clear solution |
| 6 | N.d. | 21.3 | Clear solution |
| 7 | 48 | N.d. | Clear solution |
| 8 | N.d. | 21.4 | Clear solution |
| 14 | 49 | 21.3 | Clear solution |

N.d. = not determined

Visual clouding of the mixture only occurred after 2.5 months.

It can be seen from Table 2 that there is no change in the NCO content, even after 2 weeks. After an initial slight increase, the viscosity remained the same in storage.

Example 3

Storage tests were carried out as in Example 2 with mixtures of 3a) 466 g of MDI and 200 g of methyl ester of a coconut oil fatty acid mixture (composition in % by weight: 6 to 9 capric acid ($C_8$), 6 to 10 captic acid ($C_{10}$), 44 to 51 lauric acid ($C_{12}$), 13 to 18 myristic acid ($C_{14}$), 8 to 10 palmitic acid ($C_{16}$), 1 to 3 stearic acid, 5.5 to 7.5 oleic acid)

3b) 466 g of MDI and 200 g of methyl ester of a rapeseed oil fatty acid mixture low in erucic acid (for composition, see Example 1)

3c) 466 g of MDI and 200 g of the methyl ester of lauric acid.

The results are set out in Table 3.

TABLE 3

Storage test

| | Example 3a | | | Example 3b | | | Example 3c | | |
|---|---|---|---|---|---|---|---|---|---|
| Days | Höppler viscosity at 20° C. (mPa · s) | NCO (% by weight) | Appearance | Höppler viscosity at 20° C. (mPa · s) | NCO (% by weight) | Appearance | Höppler viscosity at 20° C. (mPa · s) | NCO (% by weight) | Appearance |
| 0 | 28 | 21.7 | Clear | 44 | N.d. | Clear | 30 | N.d. | Clear |
| 5 | 28 | N.d. | Clear | 45 | N.d. | Clear | 30 | N.d. | Clear |
| 6 | N.d. | 21.7 | Clear | N.d. | 21.5 | Clear | N.d. | 21.5 | Clear |
| 7 | 29 | N.d. | Clear | 45 | N.d. | Clear | 30 | N.d. | Clear |
| 8 | N.d. | 21.7 | Clear | N.d. | 21.6 | Clear | N.d. | 21.9 | Clear |
| 14 | 29 | 21.9 | Clear | 46 | 21.9 | Clear | 30 | 22.3 | Clear |

N.d. = not determined

Example 4

4a) 30 g of the acetic acid ester of technical unsaturated $C_{18}$ fatty alcohol (composition in % by weight: 0–2 $C_{12}$; 1–6 $C_{14}$; 8–18 $C_{16}$; 70–83 $C_{18}'$, 0–3 $C_{20}$)

4b) 30 g of caprylic acid octyl ester were added to 70 g of MDI (Höppler viscosity at 20° C.: 370 mPa.s). The viscosity of the clear mixtures 4a and 4b was determined after 14 days with the following results: 4a) 37 mPa. s; 4b) 57 mPa.s.

We claim:

1. A process for reducing the viscosity of at least one member selected from the group consisting of isocyanates and isocyanurates comprising: adding to said member at least one ester selected from the group consisting of esters of $C_{6-22}$ fatty acids with monohydric alcohols and esters of $C_{6-22}$ fatty alcohols with monocarboxylic acids, said esters being a liquid at room temperature wherein the ratio by weight of the ester added to the member is from 5:95 to 80:20.

2. The process as claimed in claim 1 wherein said at least one ester is selected from the group consisting of esters of fatty acids with $C_{1-22}$ aliphatic alcohols.

3. The process as claimed in claim 1 wherein said at least one ester is selected from the group consisting of esters of fatty acids with $C_{1-12}$ aliphatic alcohols.

4. The process as claimed in claim 1 wherein said at least one ester is selected from the group consisting of methyl esters.

5. The process as claimed in claim 1 wherein said at least one ester is selected from the group consisting of esters of fatty alcohols with $C_{2-22}$ aliphatic monocarboxylic acids.

6. The process as claimed in claim 1 wherein said at least one ester is selected from the group consisting of esters of fatty alcohols with $C_{2-12}$ aliphatic monocarboxylic acids.

7. The process as claimed in claim 1 wherein said at least one member is selected from the group consisting of aromatic diisocyanates.

8. The process as claimed in claim 1 wherein said at least one ester is added in a ratio by weight to said member of 5:95 to 50:50.

9. The process as claimed in claim 1 wherein said at least one member is selected from the group consisting of diisocyanates, triisocyanates, tetraisocyanates and prepolymers thereof containing 2 to 4 isocyanate groups.

10. The process of claim 9 wherein the ratio is from 5:95 to 50:50.

11. A composition of matter consisting essentially of a solution containing a ratio by weight of from 5:95 to 80:20 of at least one ester selected from the group consisting of esters of $C_{6-22}$ fatty acids with monohydric alcohols and esters of $C_{6-22}$ fatty alcohols with monocarboxylic acids, said esters being a liquid at room temperature to at least one member selected from the group consisting of isocyanates and isocyanurates.

12. The composition as claimed in claim 1 wherein said at least one ester is selected from the group consisting of esters of fatty acids with $C_{1-22}$ aliphatic alcohols.

13. The composition as claimed in claim 1 wherein said at least one ester is selected from the group consisting of esters of fatty acids with $C_{1-12}$ aliphatic alcohols.

14. The composition as claimed in claim 1 wherein said at least one ester is selected from the group consisting of methyl esters.

15. The composition as claimed in claim 1 wherein said at least one ester is selected from the group consisting of esters of fatty alcohols with $C_{2-22}$ aliphatic monocarboxylic acids.

16. The composition as claimed in claim 1 wherein said at least one ester is selected from the group consisting of esters of fatty alcohols with $C_{2-22}$ aliphatic monocarboxylic acids.

17. The composition as claimed in claim 1 wherein said at least one member is selected from the group consisting of diisocyanates, triisocyanates, tetraisocyanates and prepolymers thereof containing 2 to 4 isocyanate groups.

18. The composition as claimed in claim 1 wherein said at least one member is selected from the group consisting of aromatic diisocyanates.

19. The composition as claimed in claim 1 wherein said at least one ester is present in a ratio by weight to said at least one member of 5:95 to 50:50.

* * * * *